(12) United States Patent
Riney

(10) Patent No.: US 6,582,518 B2
(45) Date of Patent: Jun. 24, 2003

(54) GUIDE SYSTEM FOR POSITIONING AN ELONGATED STRAND IN A LIQUID DISPENSING ENVIRONMENT

(75) Inventor: John M. Riney, Buford, GA (US)

(73) Assignee: Nordson Corporation, Westlake, OH (US)

( * ) Notice: Subject to any disclaimer, the term of this patent is extended or adjusted under 35 U.S.C. 154(b) by 126 days.

(21) Appl. No.: 09/816,522

(22) Filed: Mar. 23, 2001

(65) Prior Publication Data
US 2002/0136833 A1 Sep. 26, 2002

(51) Int. Cl.⁷ .................................................. B05C 5/00
(52) U.S. Cl. ....................................... 118/325; 118/313
(58) Field of Search .......................... 242/615.2, 615.3, 242/157 R; 226/192, 191, 179, 180; 65/529, 453; 118/420, 325, 315, 313; 427/424, 256, 207.1, 208.2, 208.4, 208.6

(56) References Cited

U.S. PATENT DOCUMENTS 3,997,308 A * 12/1976 Drummond et al.
4,048,861 A * 9/1977 Woidke et al.
4,222,758 A * 9/1980 Stotler et al.
6,067,928 A * 5/2000 Holzer et al. ............... 118/420
6,077,375 A   6/2000 Kwok

FOREIGN PATENT DOCUMENTS

EP    1176232    * 1/2002

OTHER PUBLICATIONS

ITW Dynatec Integra "Elastic Strand Coating System" Web Page Copyright 1998 (pp. 1–3).*

* cited by examiner

Primary Examiner—Brenda A. Lamb
(74) Attorney, Agent, or Firm—Wood, Herron & Evans, LLP

(57) ABSTRACT

A guide system and method for positioning an elongated strand in a liquid dispensing environment. The guide system includes a guide mechanism for supporting and guiding the strand in alignment with a dispensing outlet of a liquid dispenser. The guide mechanism is adjustable along three orthogonal axes. A bead of liquid material is dispensed from the dispensing outlet that is fully or at least partially captured on the strand.

13 Claims, 4 Drawing Sheets

GUIDE SYSTEM FOR POSITIONING AN ELONGATED STRAND IN A LIQUID DISPENSING ENVIRONMENT

FIELD OF THE INVENTION

The present invention relates generally to liquid dispensing systems for dispensing liquid material onto an elongated strand and, more particularly, to a guide system for use with such a liquid dispensing system to guide the strand during the dispensing process.

BACKGROUND OF THE INVENTION

In the manufacture of disposable diapers, adult incontinence pads and other hygienic articles, it is often desirable to provide a stretchable portion on the article, such as a waist band, leg cuff or other stretchable area, so that a relatively tight fluid seal between the article and the body can be formed. Generally, these stretchable portions are formed either by bonding stretched elastic strands directly to the fabric, or by bonding stretched elastic bands directly to a web of waist band or leg cuff material, for example, which is then bonded to selected areas of the article. The stretched elastic strands are bonding to the substrate substantially entirely along their respective axial lengths so that as the strands contract, the substrate is bunched together to form stretchable fabrics for use in a variety of products.

During the liquid dispensing process, the strands run continuously in a machine direction while the liquid dispensing system dispenses beads of adhesive toward the strands. Each bead may be dispensed in a swirl pattern toward a strand so that the pattern of the dispensed bead expands in the cross-machine direction. The dispensed pattern is controlled so that a portion of the bead crosses the travel path of the strand and attaches thereto.

Proper coating of the strands with adhesive material requires proper positioning of the strands relative to the dispensing outlets of the liquid dispenser. For example, if the distance between the strands and the dispensing outlets is too great, the dispensed adhesive beads will have pattern widths that will overshoot the edges of the strands so that portions or amounts of the dispensed adhesive material may be wasted. Also, if each strand is not generally aligned in the cross-machine direction with the axis of a respective dispensing outlet, the dispensed adhesive beads will not be applied symmetrically to the strand so that portions of the strand may not receive adhesive and therefore will not be properly laminated to the substrate.

In the past, a rotatable guide wheel has been mounted to the liquid dispensing system upstream of the dispensing outlets to guide the strands along travel paths spaced from the respective dispensing outlets. The guide wheel has circumferential grooves that engage and support the strands to guide the strands along their respective travel paths. In one known approach, the guide wheel is mounted to the liquid dispensing system through a rigid support arm that positions the guide wheel, and thus the travel paths of the strands, at fixed locations relative to the dispensing outlets. Therefore, no adjustability is provided to change the position of the strands relative to the dispensing outlets. In another known approach, the guide wheel is mounted to the liquid dispensing system through a linkage assembly having two (2) degrees of freedom that permits adjustments to be made in the position of the guide wheel in the machine direction, and in the distance between the strands and their respective dispensing outlets by raising or lowering of the guide wheel. Neither of these approaches provides manual adjustability of the positioning of the strands in the cross-machine direction so that the strands can be accurately and reliably aligned with the axes of their respective dispensing outlets to ensure proper coating of the strands prior to lamination.

Accordingly, there is a need for a guide system that improves the positioning of an elongated strand relative to a dispensing outlet of a liquid dispenser.

SUMMARY OF THE INVENTION

The present invention overcomes the foregoing and other shortcomings and drawbacks of guide systems and methods heretofore known for positioning elongated strands in a liquid dispensing environment. While the invention will be described in connection with certain embodiments, it will be understood that the invention is not limited to these embodiments. On the contrary, the invention includes all alternatives, modifications and equivalents as may be included within the spirit and scope of the present invention.

The guide system of the present invention positions one or more elongated strands of material relative to dispensing outlets of a liquid dispensing system. The strands may comprise elastic or non-elastic materials. Each strand travels along a travel path spaced from a respective dispensing outlet so that a bead of adhesive is fully or at least partially captured on the strand prior to the strand being bonded to a substrate.

The strands run continuously in a machine direction, and the liquid dispensing system is operable to dispense beads of adhesive toward the strands from the respective dispensing outlets. Each bead is preferably dispensed in a swirl pattern toward the strand so that the pattern expands in the cross-machine direction and a portion of the bead crosses the travel path of the strand and attaches thereto.

The guide system of the present invention includes a guide mechanism, preferably in the form of a rotatable wheel having circumferential grooves that are operable to guide the strands along travel paths generally in alignment with the respective dispensing outlets so that the travel path of each strand generally intersects the axis of a respective dispensing outlet. The guide system further includes a positioning mechanism operatively connected to the guide mechanism for positioning the guide mechanism along three (3) orthogonal axes, namely an X-axis in the machine direction, a Y-axis, and a Z-axis in the cross-machine direction. The guide system has three (3) degrees of freedom for positioning the guide mechanism along the three (3) orthogonal axes. The guide mechanism engages and supports the strands upstream of the dispensing outlets and controls the position of each strand along a Z-axis, i.e., the position of the strand in the cross-machine direction relative to the axis of a respective dispensing outlet, and along a Y-axis, i.e, the spacing or distance of each strand from a respective dispensing outlet. The positioning mechanism is operable to properly position the guide mechanism upstream of the dispensing outlets so that the position of the guided strands relative to the respective dispensing outlets can be accurately and reliably adjusted and controlled.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE PREFERRED EMBODIMENT

Figure 1:
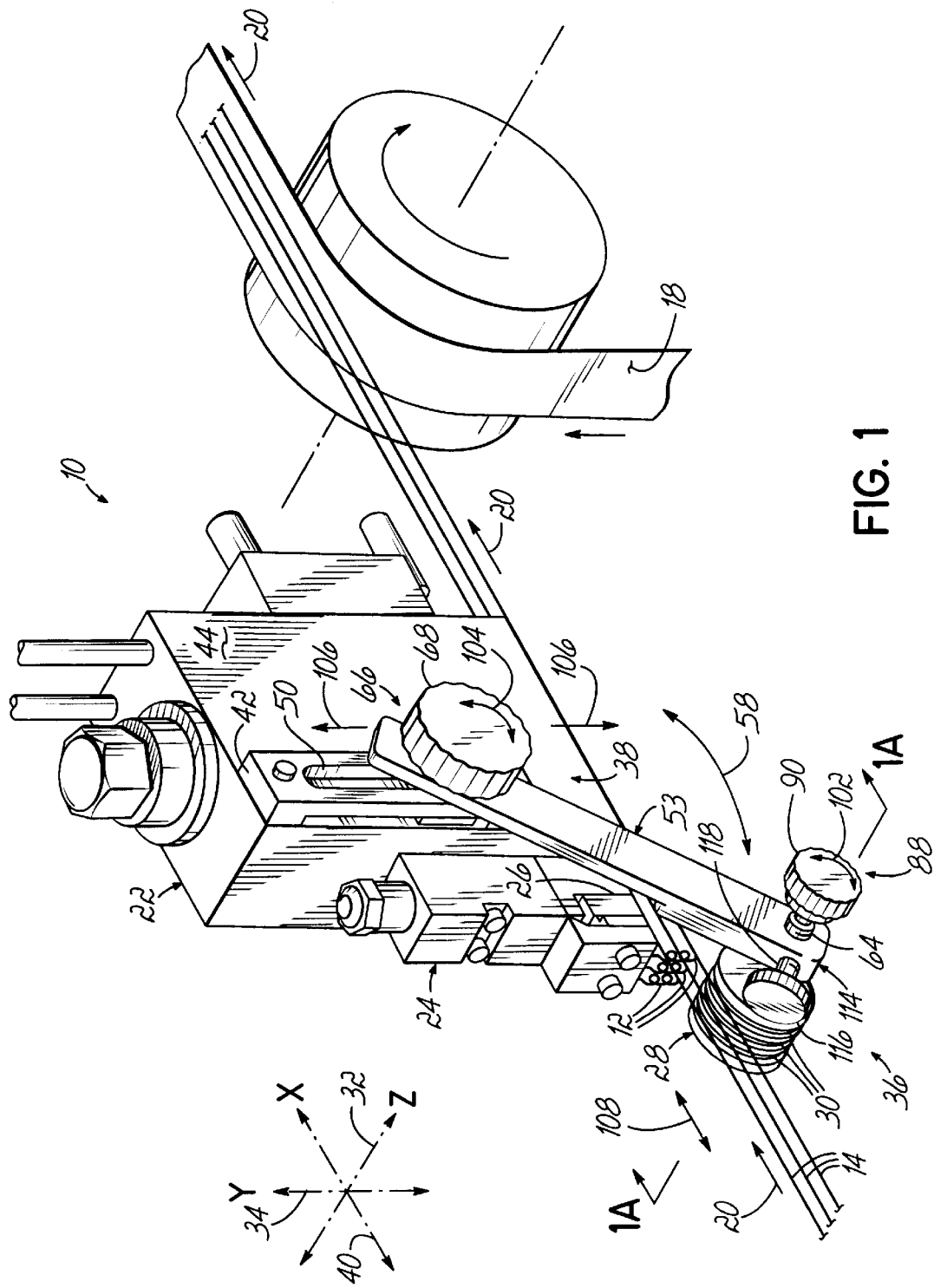
FIG. 1 is a perspective view of a guide system in accordance with the principles of the present invention, illustrating the guide system in use for positioning elongated strands relative to dispensing outlets of a liquid dispenser.

With reference to the Figures, and to FIG. 1 in particular, a liquid dispensing system 10 is shown in accordance with the principles of the present invention for dispensing beads of liquid material, such as beads 12 of hot melt adhesive, onto elongated strands 14, such as strands of elastic or non-elastic material. As will described in greater detail below, each of the strands 14 travels along a travel path spaced from a respective dispensing outlet 16 (FIG. 1A) of the liquid dispensing system 10 so that a bead 12 of adhesive is fully or at least partially captured on each strand 14 while each strand 14 is separate from a substrate 18, such as a web of waist band or leg cuff material used in the manufacture of diapers (not shown) for example. The coated elastic strands 14, which may comprise elastic strands of LYCRA XA™ Spandex, a synthetic stranded product manufactured by DuPont, or other stranded elastic products such as threaded natural rubber by way of example, are thereafter bonded to the substrate 18 substantially entirely along their respective axial lengths so that as the strands 14 contract, the web 18 is bunched together to form the stretchable waist bands, leg cuffs or other stretchable fabrics for a variety of products. The term "strand" or similar terms used in the present specification are meant to include both elastic and non-elastic materials.

Further referring to FIG. 1, the strands 14 run continuously in a machine direction (MD), represented by arrows 20. The liquid dispensing system 10 is operable to receive hot melt adhesive from a liquid adhesive source (not shown), and to dispense the beads 12 of adhesive toward the strands 14 from the respective dispensing outlets 16. While three (3) parallel elongated strands 14 are shown being coated by beads 12 of material dispensed from three (3) liquid dispensing outlets 16 (FIG. 1A), one or multiple strands 14 can be used and the adhesive can be dispensed from one or multiple dispensing outlets 16.

The liquid dispensing system 10 includes an adhesive and air manifold 22 connected to a liquid dispensing module 24 in a manner known to those of ordinary skill in the art. The liquid dispensing module 24 may include an internal valve (not shown) for controlling the flow of adhesive through the dispensing outlets 16, and has a pattern die 26 (FIG. 1) connected at a remote end of the dispensing module 24 that controls the pattern of each adhesive bead 12 dispensed from a respective outlet 16.

The pattern die 26 may comprise a SuMMit™ pattern die commercially available from Nordson Corporation of Westlake, Ohio, assignee of the present invention, and fully described in detail in U.S. Ser. No. 09/571,703, filed May 15, 2000, which is incorporated herein by reference in its entirety. By way of background, the SuMMit™ pattern die is configured with multiple dispensing outlets 16 arranged along the width of the pattern die 26, with each liquid dispensing outlet 16 having four (4) air outlets (not shown) arranged around the dispensing outlet 16 forming four (4) radially tangential air jets (not shown) that spin the dispensed bead 12 of adhesive in a generally symmetrical spiral pattern toward the strand 14. The operating characteristics of the liquid dispensing system 10, including the adhesive pressure, air pressure, distance from the dispensing outlet 16 to the strand 14, can all be varied to control the extent of the adhesive wrap around and to control the amount of adhesive captured by the strand 14. The adhesive bead 12 is dispensed toward the strand 14 in a generally symmetrical pattern relative to the axis of the outlet 16 so that the pattern expands in the cross-machine direction (CD). The strand 14 travels in the machine direction (MD) so that at least a portion of the bead 12 crosses the travel path of the strand 14 and attaches thereto.

Figure 1A:
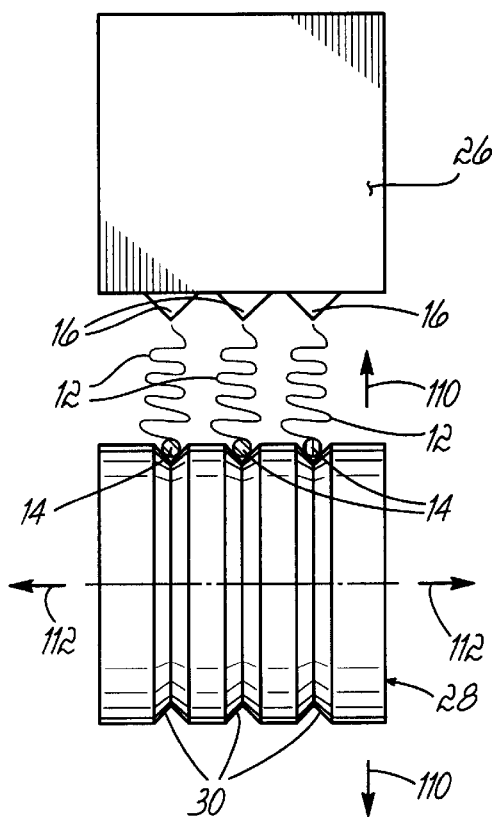
FIG. 1A is a cross-sectional view taken along line 1A—1A of FIG. 1.

As shown in FIGS. 1 and 1A, the strands 14 are guided along their respective travel paths by a guide mechanism 28, preferably in the form of a rotatable wheel having circumferential grooves 30 that are operable to guide the stands 14 generally in alignment with the respective dispensing outlets 16 so that the travel path of each strand 14 generally intersects the axis of a respective dispensing outlet 16, as shown in FIG. 1A. The guide mechanism 28 engages and supports the strands 14 upstream of the dispensing outlets 16 and controls the position of each strand 14 along a Z-axis 32, i.e., the position of each strand 14 in the cross-machine direction (CD) relative to the axis of a respective dispensing outlet 16, and along a Y-axis 34, i.e., the spacing or distance of each strand 14 from a respective dispensing outlet 16. Accurate positioning of each stand 14 relative to its respective dispensing outlet 16 along the Y- and Z-axes 34, 32 is critical for achieving a coating of adhesive on each strand 14 that will permit the strand 14 to be bonded substantially entirely along its axial length to the web 18. For example, if each strand 14 is spaced too far along the Y-axis 34 from its respective dispensing outlet 16, the dispensed bead 12 will have a pattern width that will overshoot the edges of the strand 14 so that a portion of the dispensed adhesive material may be wasted. Additionally, if each strand 14 is not generally aligned with the axis of its respective dispensing outlet 16 along the Z-axis 32, the dispensed bead 12 of adhesive will not be applied symmetrically to the strand 14 so that portions of the strand 14 may not be properly laminated to the web 18.

Figure 2A:
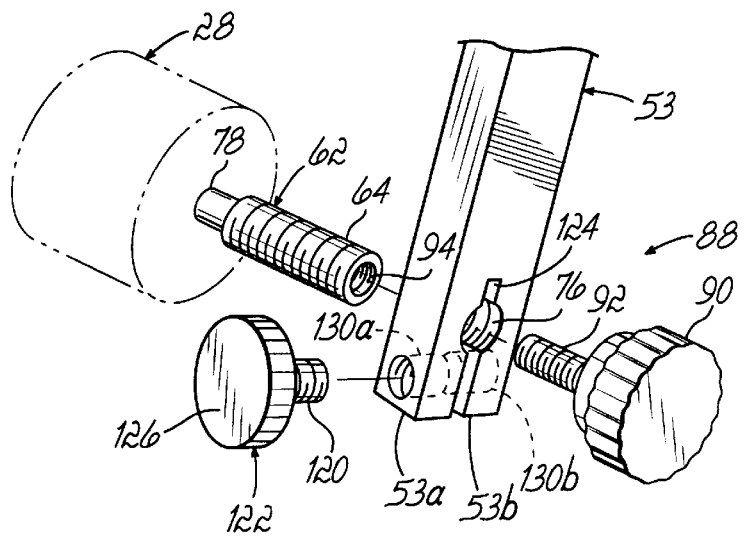
FIG. 2A is an enlarged perspective view of an alternative set mechanism provided on the guide system of FIG. 1.
Figure 2:
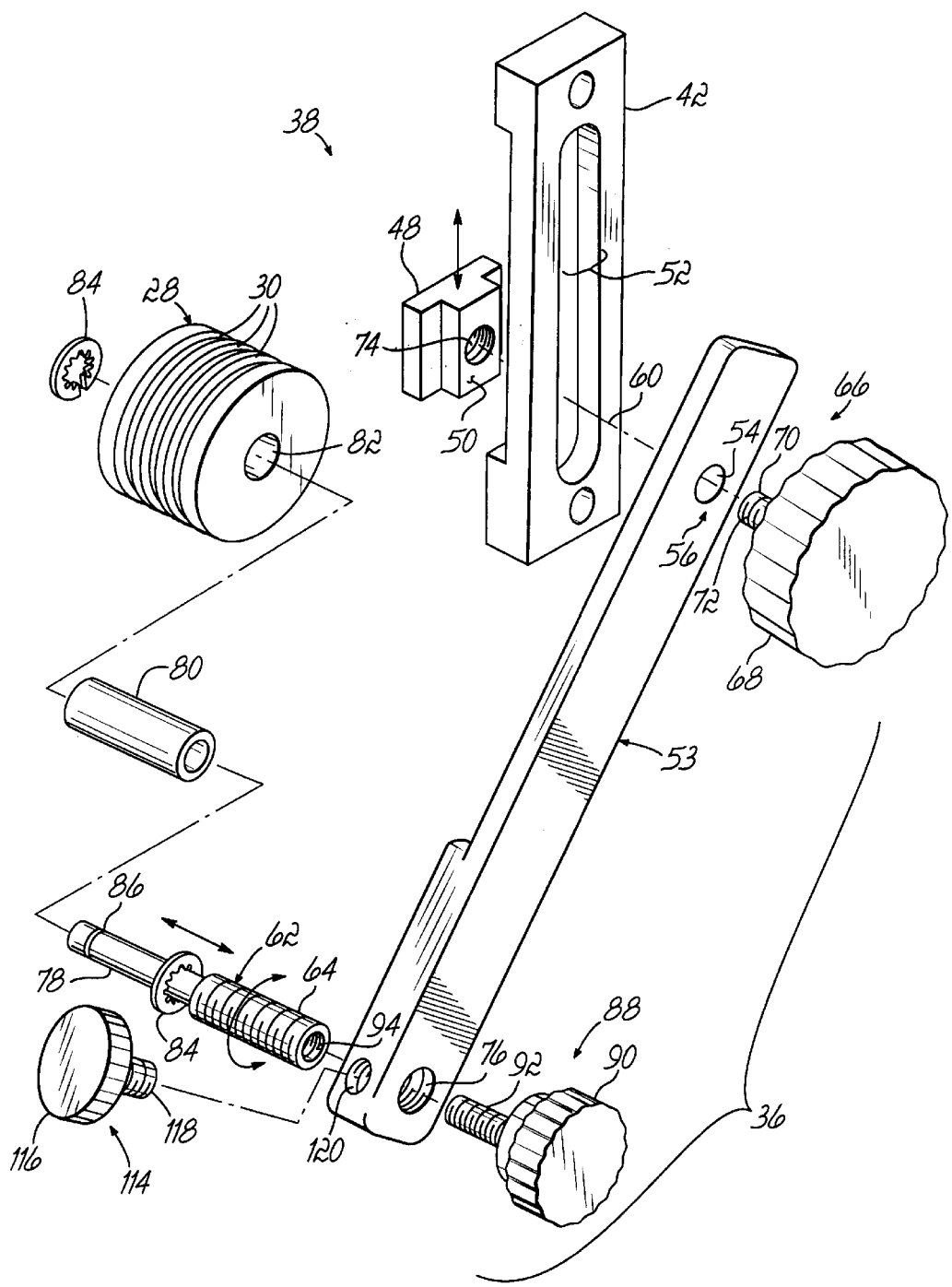
FIG. 2 is a disassembled perspective view of the guide system shown in FIG. 1, illustrating a guide mechanism of the guide system in accordance with one embodiment of the present invention.

Referring now to FIGS. 1 and 2, a guide system 36 in accordance with the principles of the present invention is shown for accurately and reliably positioning the elongated strands 14 relative to their respective dispensing outlets 16. The guide system 36 includes a positioning mechanism 38 operatively connected to the adhesive and air manifold 22 and the guide mechanism 28 for positioning the guide mechanism 28 along three (3) orthogonal axes, namely an X-axis 40 in the machine direction (MD), the Y-axis 34, and the Z-axis 32 in the cross machine direction (CD). As will be described in greater detail below, the guide system 36 has three (3) degrees of freedom for positioning the guide mechanism 28 along the three (3) orthogonal axes 32, 34 and 40. In this way, the positioning mechanism 38 is operable to properly position the guide mechanism 28 upstream of the dispensing outlets 16 so that the position of the guided strands 14 relative to the respective dispensing outlets 16 can be accurately and reliably adjusted and controlled.

In one embodiment of the present invention, as shown in FIGS. 1 and 2, the positioning mechanism 38 includes an elongated guide member 42 that is mounted to a side surface 44 of the adhesive and air manifold 22. Of course, it will be appreciated by those skilled in the art that other orientations and mountings of the guide member 42 are possible without departing from the spirit and scope of the present invention. For example, it is contemplated that the guide member 42 may be mounted to a front surface 46 of the adhesive and air manifold 22 or, alternatively, the guide member 42 may be supported by a support stand (not shown) this is entirely separated from, but mounted in the general area of, the liquid dispensing system 10.

The guide member 42 retains and guides a T-nut 48 having a boss 50 free to travel within an elongated slot 52 formed in the guide member 42 so that the T-nut 48 is free to travel relative to the guide member 42 along the Y-axis 34. The positioning mechanism 38 further includes an elongated arm member 53 having an unthreaded bore 54 (FIG. 2) extending through the arm member 53 that forms a pivotal connection 56. As will be described in detail below, the pivotal connection 56 permits the arm member 53 to be rotated relative to the guide member 42, as indicated generally by arrow 58 in FIG. 1, about an axis 60 of the pivotal connection 56 (see FIG. 2). The pivotal connection 56 is capable of linear movement relative to the guide member 42 along the Y-axis 34. A shaft member 62 is operatively connected to the guide mechanism 28 and has a threaded end 64 (FIG. 2) operatively connected to the arm member 53 at a position remote from the pivotal connection 56. As will be described in greater detail below, the shaft member 62 and guide mechanism 28 are mounted to the arm member 53 for linear movement along the Z-axis 32.

Further referring to FIGS. 1 and 2, an adjustment mechanism 66, including a manually rotatable knob 68 and a partially threaded shaft 70, is provided to operatively connect the arm member 53 to the guide member 42. The partially threaded shaft 70 extends through the pivotal connection 56 in arm member 53 and the elongated slot 52 in guide member 42 so that a threaded portion 72 (FIG. 2) of the shaft 70 engages a threaded bore 74 (FIG. 2) in the T-nut 48. An unthreaded portion (not shown) of the shaft 70 engages the pivotal connection 56 of the arm member 53 so as to permit the arm member 53 to rotate about the unthreaded portion (not shown) of the shaft 70.

As shown in FIG. 2, the threaded end 64 of shaft member 62 engages a threaded bore 76 formed through the arm member 53 at a position remote from the pivotal connection 56. The shaft member 62 includes an unthreaded portion 78 of reduced diameter for supporting a bearing sleeve 80 and the guide mechanism 28. More particularly, in the embodiment of FIG. 2, the bearing sleeve 80 is received within an axial bore 82 of the guide mechanism 28. The bearing sleeve 80 and guide mechanism 28 are captured on the unthreaded portion 28 of shaft member 62 by a pair of retaining rings 84 that are retained in a pair of spaced circumferential grooves 86 (one shown in FIG. 2) formed on the unthreaded portion 78 of the shaft member 62. The retaining rings 84 prevent axial movement of the bearing sleeve 80 and the guide mechanism 28 along the unthreaded portion 78 of the shaft member 62.

Further referring to FIGS. 1 and 2, an adjustment mechanism 88, including a manually rotatable knob 90 and a threaded shaft 92, is provided to rotate the shaft member 62 in the threaded bore 76 formed in the arm member 53. The threaded shaft 92 of the adjustment mechanism 88 has a diameter that is less than that of the threaded bore 76 in the arm member 53. The threaded shaft 92 is received in a threaded bore 94 formed in the threaded end 64 of the shaft member 62. The threaded shaft portion 64 of shaft member 62 has an outer diameter that generally equals the inner diameter of the threaded bore 76 formed in arm member 53, and an inner diameter that generally equals the outer diameter of the threaded shaft 92 of adjustment mechanism 88.

Figure 3:
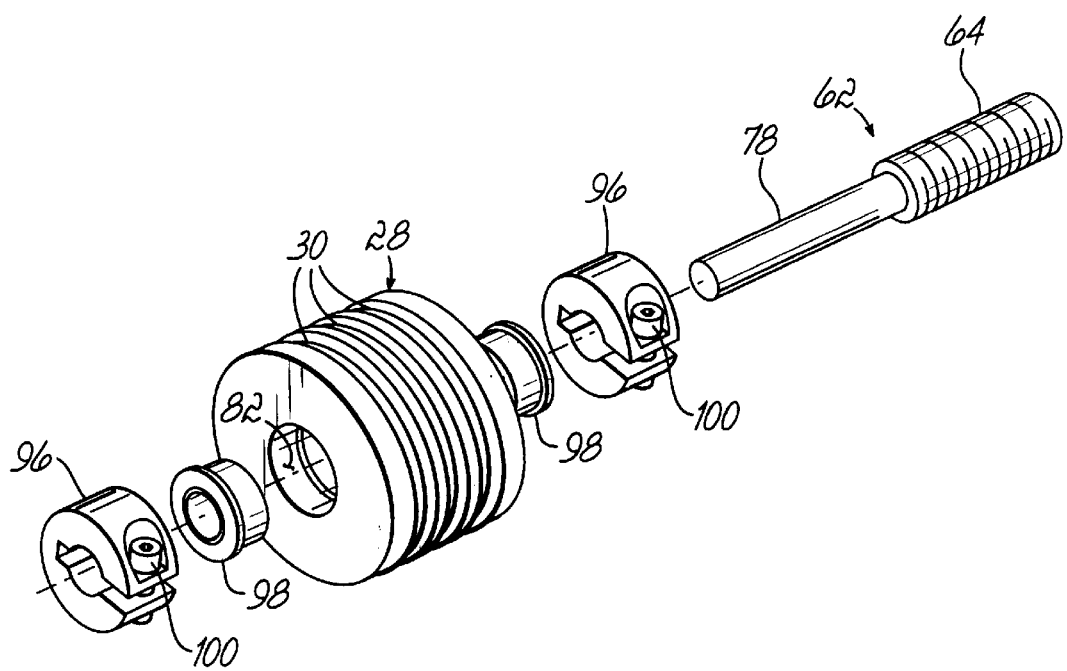
FIG. 3 is a disassembled perspective view of a guide mechanism in accordance with an alternative embodiment of the present invention.

Alternatively, in the embodiment shown in FIG. 3, where like numerals represent like parts, the retaining rings 84 and bearing sleeve 80 described above in connection with FIG. 2 are replaced, respectively, with a pair of retaining collars 96 and a pair of roller bearings 98 that are press-fit into opposite ends of the axial bore 82 formed in the guide mechanism 28. Each of the retaining collars 96 includes a set screw 100 that enables the axial position of each retaining collar 96 on the unthreaded portion 78 of the shaft member 62 to be set. The retaining collars 96 are positioned and set to prevent axial movement of the guide mechanism 28 along the unthreaded portion 78 of shaft member 62.

In use of the guide system 36, the guide mechanism 28 is adjusted along the three (3) orthogonal axes 32, 34, 40 through manual adjustment of the adjustment mechanisms 66 and 88, as represented by respective arrows 102 and 104 in FIG. 1. Adjustment of the guide mechanism 28 along the X- and Y-axes 40, 34 is provided by adjustment mechanism 66, while adjustment of the guide mechanism 28 along the Z-axis 32 is provided by adjustment mechanism 88. In particular, when the rotatable knob 68 of adjustment mechanism 66 is manually loosened to release frictional engagement of the arm member 53 with the guide member 42, the pivotal connection 56 of the arm member 53 is able to be adjusted along the Y-axis 34 through movement of the knob 68, partially threaded shaft 70 and T-nut 48 along the Y-axis 34, as represented by arrows 106 in FIG. 1. The rotational position of the arm member 53 relative to the guide member 42 is able to be simultaneously adjusted when the knob 68 is loosened, as represented by arrow 58 in FIG. 1. It will be appreciated by those skilled in the art that movement of the pivotal connection 56 along the Y-axis 34 and rotation of the arm member 53 relative to the guide member 42 provide adjustment of the guide mechanism 28 along the X- and Y-axes 40, 34, as represented by arrows 108 and 110, respectively in FIGS. 1 and 1A. When the desired position of the guide mechanism 28 has been obtained along the X- and Y-axes 40, 34, the knob 68 is again tightened to frictionally engage the arm member 53 with the guide member 42 to secure the guide mechanism 28 in place.

Adjustment of the guide mechanism 28 along the Z-axis 32 is provided by manually rotating knob 90 operatively connected to the shaft member 62, as represented by arrow 102 in FIG. 1. In particular, when the rotatable knob 90 of adjustment mechanism 88 is rotated, the threaded end 64 of shaft member 62 rotates in the threaded bore 76 formed in the arm member 53 to provide linear movement of the shaft member 62 and guide mechanism 28 along the Z-axis 32, as represented by arrows 112 in FIG. 1A. A set mechanism 114 (FIGS. 1 and 2), including a knob 116 and a threaded shaft 118, is provided to set or lock the position of the shaft member 62 relative to the arm member 53. The threaded shaft 118 of set mechanism 114 is received in a threaded bore 120 formed in the arm member 53 and engages the threaded shaft 64 of shaft member 62 when the knob 116 is tightened.

Alternatively, as shown in FIG. 2A, where like numerals represent like parts, the set mechanism 114 described above in connection with FIG. 2 is replaced with a modified set mechanism 122. In this embodiment, the arm member 53 includes an elongated slit 124 along its longitudinal axis that intersects the threaded bore 76 and bifurcates the remote end of the arm member 53 into a pair of compressible fingers 53a, 53b. The set mechanism 122 includes a knob 126 and a threaded shaft 128 that is received in aligned bores 130a, 130b formed in each of the fingers 53a, 53b. An unthreaded bore 130a is formed near the end of finger 53a, and a threaded bore 130b is formed near the end of finger 53b so that the fingers 53a, 53b can be firmly clamped around the shaft member 62 to set or lock its position when the knob 126 is tightened.

Those skilled in the art will appreciate that the guide system 36 of the present invention has three degrees of freedom. The first degree of freedom is provided by linear movement of the pivotal connection 56 along the Y-axis 34. The second degree of freedom is provided by rotation of the arm member 53 relative to the guide member 42 about the axis 60 of the pivotal connection 56. Lastly, the third degree of freedom is provided by linear movement of the shaft member 62 and guide mechanism 28 along the Z-axis 32. The guide system 36 of the present invention permits adjustment of the position of the guide mechanism 28 along each of three (3) orthogonal axes 32, 34, 40, with particularly fine or micro-adjustment of the position of the guide mechanism 28 along the Z-axis 32. The guide system 36 provides the adjustment capability without the need for tools so that simple, accurate and reliable position control of the strands 14 is provided. Further, it will be appreciated that guide system 36 is configured to be mounted on either side of the liquid dispensing system 10. Of course, while the connection of the arm member 53 to the guide member 42 forms one type of linkage assembly that provides positioning of the guide mechanism 28 along the X- and Y-axes 40, 34, those of ordinary skill in the art will appreciate that other linkage assemblies are possible as well that will provide substantially the same function.

For example, while not shown, it is contemplated that the positioning mechanism 38 may comprise two (2) pivotal arms having two degrees of freedom. One pivotal arm has a pivotal connection at one end of the arm that is pivotally connected to the liquid dispensing system 10. A second pivotal connection is provided at an opposite end of the one pivotal arm to pivotally connect the opposite end of the first arm to one end of a second pivotal arm. The two (2) degrees of freedom are provided by the two (2) pivotal connections of the two pivotal arms. The guide mechanism 28 may be operatively connected to a shaft mounted to an opposite end of the second pivotal arm to provide adjustment of the guide mechanism 28 in the Z-axis 32. Other linkage structures will be readily appreciated by those of ordinary skill in the art without departing from the spirit and scope of the present invention.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicants' general inventive concept.

Having described the invention, what is claimed is:

1. A guide system for positioning an elongated strand relative to a dispensing outlet capable of dispensing liquid material onto the strand, comprising:

a guide mechanism capable of guiding the strand along a travel path spaced from the dispensing outlet; and a positioning mechanism operatively connected to said guide mechanism for moving said guide mechanism along three orthogonal axes to position the strand relative to the dispensing outlet for dispensing liquid material thereon, said positioning mechanism comprising:

an elongated guide member;

an elongated arm member having a pivotal connector operatively connected to said guide member for permitting rotation of said arm member relative to said guide member about a first axis;

said pivotal connector being mounted to said guide member permitting linear movement of said arm member and said pivotal connector relative to said guide member along a second axis transverse to said first axis; and a shaft member having first and second ends, said first end operatively connected to said guide mechanism and said second end operatively connected to said arm member at a location remote from said pivotal connector permitting linear movement of said shaft member and said guide mechanism along a third axis tranverse to said second axis.

2. The guide system of claim 1, wherein said guide mechanism is mounted for rotation on said shaft member.

3. The guide system of claim 2, wherein said guide mechanism comprises a rotatable wheel having a circumferential groove formed therein capable of guiding the strand along the travel path.

4. The guide system of claim 2, wherein said shaft member is threadably connected to said arm member to provide the linear movement of said shaft member and said guide mechanism along said third axis upon rotation of said shaft member.

5. The guide system of claim 1, further comprising:

a first adjustment mechanism operatively connected to said guide member and said arm member, and configured to permit simultaneous adjustment in the rotation of said arm member relative to said guide member about said first axis and in the linear movement of said pivotal connection relative to said guide member along said second axis.

6. The guide system of claim 5, wherein said first adjustment mechanism comprises:

a rotatable knob having a shaft extending through said pivotal connection of said arm member; and a nut guided by said guide member for movement along the second axis and operatively connected to said shaft.

7. The guide system of claim 1, further comprising:

a second adjustment mechanism operatively connected to said second end of said shaft member and said arm member, and configured to provide adjustment in the linear movement of said shaft member and said guide mechanism along said third axis.

8. The guide system of claim 7, wherein said second adjustment mechanism comprises:

a rotatable knob having a shaft extending through said arm member and operatively connected to the one end of said shaft member.

9. A liquid dispensing system for dispensing liquid onto an elongated strand, comprising:

a liquid dispenser having a dispensing outlet capable of dispensing liquid material onto the strand;

a guide mechanism capable of guiding the strand along a travel path spaced from said dispensing outlet; and a positioning mechanism operatively connected to said guide mechanism and said liquid dispenser for moving said guide mechanism along three orthogonal axes to position the strand relative to said dispensing outlet for dispensing liquid material thereon, said positioning mechanism comprising:

an elongated guide member;

an elongated arm member having a pivotal connector operatively connected to said guide member for permitting rotation of said arm member relative to said guide member about a first axis;

said pivotal connector being mounted to said guide member permitting linear movement of said arm member and said pivotal connector relative to said guide member along a second axis transverse to said first axis; and a shaft member having first and second ends, said first end operatively connected to said guide mechanism and said second end operatively connected to said arm member at a location remote from said pivotal connector permitting linear movement of said shaft member and said guide mechanism along a third axis transverse to said second axis.

10. The guide system of claim 9, further comprising:

a first adjustment mechanism operatively connected to said guide member and said arm member at said pivotal connection, and configured to permit simultaneous adjustment in the rotation of said arm member relative to said guide member about said first axis and in the linear movement of said pivotal connection relative to said guide member along said second axis.

11. The guide system of claim 10, wherein said first adjustment mechanism comprises:

a rotatable knob having a shaft extending through said pivotal connection of said arm member; and a nut guided by said guide member for movement along the second axis and operatively connected to said shaft.

12. The guide system of claim 9, further comprising:

a second adjustment mechanism operatively connected to said second end of said shaft member and said arm member, and configured to provide adjustment in the linear movement of said shaft member and said guide mechanism along said third axis.

13. The guide system of claim 12, wherein said second adjustment mechanism comprises:

a rotatable knob having a shaft extending through said arm member and operatively connected to the one end of said shaft member.

\* \* \* \* \*